US010067140B2

(12) United States Patent
Ozbal

(10) Patent No.: US 10,067,140 B2
(45) Date of Patent: Sep. 4, 2018

(54) MASS-SPECTROMETER SYSTEMS AND METHODS

(71) Applicant: PureHoney Technologies, Inc., Acton, MA (US)

(72) Inventor: Can Ozbal, Lexington, MA (US)

(73) Assignee: PureHoney Technologies, Inc., Billerica, MA (US)

( * ) Notice: Subject to any disclaimer, the term of this patent is extended or adjusted under 35 U.S.C. 154(b) by 0 days.

(21) Appl. No.: 15/352,066

(22) Filed: Nov. 15, 2016

(65) Prior Publication Data
US 2017/0059580 A1    Mar. 2, 2017

Related U.S. Application Data

(63) Continuation of application No. 14/594,060, filed on Jan. 9, 2015, now Pat. No. 9,494,497.
(Continued)

(51) Int. Cl.
*H01J 1/34* (2006.01)
*A61B 5/157* (2006.01)
(Continued)

(52) U.S. Cl.
CPC ........... *G01N 33/6848* (2013.01); *G01N 1/34* (2013.01); *G01N 33/9446* (2013.01); *G01N 35/1097* (2013.01); *G01N 2001/4088* (2013.01)

(58) Field of Classification Search
USPC ......... 250/281, 282, 288, 428, 430, 432 PD, 250/526; 600/309, 317, 321; 604/65–67,
(Continued)

(56) References Cited

U.S. PATENT DOCUMENTS

| 6,177,008 B1 * | 1/2001 | Treiber | B01D 15/08 |
| | | | 210/198.2 |
| 6,812,030 B2 * | 11/2004 | Ozbal | B01F 5/0085 |
| | | | 210/656 |

(Continued)

OTHER PUBLICATIONS

Dwivedi Somya, et al. "Characterization of *Arabidopsis thaliana* mutant ror-1 (roscovitine-resistant) and its utilization in understanding of the role of cytokinin N-glucosylation pathway in plants." Plant growth regulation 61.3 (2010): 231-242.

*Primary Examiner* — Bernard Souw
(74) *Attorney, Agent, or Firm* — Mintz Levin Cohn Ferris Glovsky and Popeo, P.C.

(57) ABSTRACT

Embodiments of the present disclosure present novel systems, devices and methods for an automated biological sample analysis using mass-spectrometry. The time from sample introduction to the reporting of data, in some embodiments, takes a relatively short amount of time (e.g., several minutes). In some embodiments, a biological sample to be analyzed is a blood sample. For many applications, only a single drop of blood may be sufficient. Through the use of a mixture of standards with unique molecular mass, a quantitative analysis of the target analyte can be performed in a single MS run (for example), eliminating the need to create and analyze standard curves. One advantage of such embodiments may be that the system, devices, and methods can eliminate the need for batch creation since the requirement to amortize the time and effort of creating and analyzing standard curves can be eliminated.

20 Claims, 5 Drawing Sheets

Related U.S. Application Data

(60) Provisional application No. 61/926,094, filed on Jan. 10, 2014.

(51) Int. Cl.
*A61M 5/172* (2006.01)
*G01N 33/68* (2006.01)
*G01N 1/34* (2006.01)
*G01N 35/10* (2006.01)
*G01N 33/94* (2006.01)
*G01N 1/40* (2006.01)

(58) Field of Classification Search
USPC ........ 604/323, 335, 504; 422/131, 140, 141, 422/500, 504, 505, 509, 513, 527, 534, 422/537, 554, 56
See application file for complete search history.

(56) References Cited

U.S. PATENT DOCUMENTS

| | | | | |
|---|---|---|---|---|
| 6,932,929 B2* | 8/2005 | Krautkramer | ......... | A61F 13/534 264/113 |
| 7,588,725 B2* | 9/2009 | Ozbal | ................ | B01F 5/0085 210/141 |
| 7,907,985 B2* | 3/2011 | Gable | ................. | A61B 5/0084 422/72 |
| 7,972,296 B2* | 7/2011 | Braig | ................. | A61B 5/1427 604/65 |
| 8,197,770 B2* | 6/2012 | Gable | ................. | A61B 5/0084 422/500 |
| 8,449,524 B2* | 5/2013 | Braig | ................. | A61B 5/1427 604/504 |
| 9,252,003 B2* | 2/2016 | Hermanson | ............ | G01N 33/60 |
| 9,289,169 B2* | 3/2016 | Rule | ................... | A61B 5/0002 |
| 9,494,497 B2* | 11/2016 | Ozbal | ............... | G01N 33/6848 |
| 9,768,001 B2* | 9/2017 | Cooper | ............... | H01J 49/0009 |
| 2002/0160521 A1* | 10/2002 | Ozbal | ................... | B01F 5/0085 436/161 |
| 2005/0219071 A1* | 10/2005 | Kajita | .................. | H04L 1/0046 341/50 |
| 2006/0014293 A1* | 1/2006 | Joyce | ................ | G01N 33/6842 436/86 |
| 2006/0189926 A1* | 8/2006 | Hall | ................... | A61B 5/14546 604/66 |
| 2007/0060872 A1* | 3/2007 | Hall | ................... | A61B 5/14546 604/66 |
| 2009/0131861 A1* | 5/2009 | Braig | ................. | A61B 5/1427 604/66 |
| 2009/0218287 A1* | 9/2009 | Vail | .................... | B01J 20/28014 210/659 |
| 2010/0015658 A1 | 1/2010 | Yang et al. | | |
| 2010/0030137 A1* | 2/2010 | Hall | ................... | A61B 5/14546 604/66 |
| 2010/0056656 A1* | 3/2010 | Matsuoka | ............... | C08L 67/04 521/96 |
| 2010/0120156 A1* | 5/2010 | Garner | .................. | G01N 33/60 436/8 |
| 2010/0256010 A1* | 10/2010 | Ozbal | ................... | G01N 30/24 506/9 |
| 2013/0295597 A1* | 11/2013 | DeWitte | ................ | G01N 30/06 435/23 |
| 2014/0058228 A1* | 2/2014 | Gable | ................. | A61B 5/0084 600/322 |
| 2015/0198501 A1* | 7/2015 | Rule | ................... | A61M 5/1413 73/40.5 R |

* cited by examiner

FLUIDIC CIRCUIT, POSITION 1: Loading and washing of sample

FLUIDIC CIRCUIT, POSITION 2: Elution of MS Analysis of Sample

FLUIDIC CIRCUIT, POSITION 1: Loading and washing of sample

FLUIDIC CIRCUIT, POSITION 2: Elution and MS analysis

TOP VIEW OF

SIDE VIEW OF

TOP VIEW OF CARTRIDGE    SIDE VIEW OF CARTRIDGE

Bottom Section           Bottom Section

Upper Section            Upper Section

MANUFACTURING PROCESS

1) Add filter or membrane to upper section

2) Add chromatography media to lower section

3) Fuse sections for completed cartridge assembly

MASS-SPECTROMETER SYSTEMS AND METHODS

CROSS-REFERENCE TO RELATED APPLICATIONS

This application is a continuation of U.S. patent application Ser. No. 14/594,060, filed Jan. 9, 2015, entitled "MASS-SPECTROMETER SYSTEMS AND METHODS," which claims priority to U.S. Provisional Application Ser. No. 61/926,094, filed Jan. 10, 2014, entitled "MASS-SPECTROMETER SYSTEMS AND METHODS," the contents of each of which are incorporated herein by reference in their entireties.

BACKGROUND

In many biomedical and healthcare applications, the rapid determination of the concentration of an analyte in a biological matrix such as blood, plasma, serum, urine, cerebrospinal fluid (CSF), or tissue extracts, is critically important. Traditionally, such measurements have been made via immunoassay-based techniques such as an enzyme linked immunosorbent assay (ELISA). Such techniques rely on the selective binding of an antibody to a target analyte within the sample. In most assays, a second antibody linked to a colorimetric, fluorometric, or radioactivity-based detection system is used to detect the analyte-antibody complex.

Many fully automated devices capable of running immunoassays on biological fluids have been developed and are commonly used in hospital and research settings. While these systems have the advantages of automation and capacity, they also have significant drawbacks. For example, the specificity and selectivity of each assay is only as good as the antibody being used. Many drugs are metabolized by the cytochrome P450 system in the liver or by other metabolic pathways. Usually the metabolite of a drug isn't active, though in certain cases a pro-drug is administered and it is the metabolite that has pharmaceutical activity. In cases where an antibody has reactivity towards both a drug and it's metabolite it is very challenging to develop an immunoassay. The cross reactivity of the antibody means that an aggregate concentration of drug and metabolite(s) will be quantified while it is only one of these species that has clinical relevance. The azole anti-fungal drugs, many anti-convulsive and anti-epileptic drugs, along with many of the calcineurin inhibitors used in transplant patients fall into this category. For classes of drugs such as benzodiazepenes, it is common for the immunoassay to react to the entire class of drugs rather than individual members of the class.

More recently many of the quantitative assays in clinical and research settings traditionally analyzed by immunosorbent assays are being analyzed by mass spectrometry-based techniques. A very common technique is the use of high-pressure liquid chromatography coupled to triple-quadrupole mass spectrometry (HPLC-MS/MS). Mass-spectrometer (MS) based assays have some significant advantages over immunosorbent assays. For example, MS assays typically have a much higher degree of selectivity for a particular analyte than immunoassay-based techniques. The MS-based assay for the determination of Vitamin D concentrations has the ability to differentiate between hydroxyl and di-hydroxy Vitamin D, an important piece of information in a clinical evaluation, while the immunoassay-based techniques are capable of quantifying total Vitamin D concentrations and cannot differentiate between the various forms.

Some mass-spectrometry based techniques may have some limitations, particularly around sample prep and the requirement to use internal standards and external calibrants for absolute quantitation. Samples that contain high concentrations of ionic strength can cause ion suppression within the source region of the mass spectrometer leading to lower signal and poor instrument response. Often samples are fractionated via chromatography, either prior to MS analysis or during the analysis itself through the use of a coupled technique such as HPLC-MS. When complex samples such as blood are being analyzed, often multiple centrifugation or extraction steps may also be required. The requirement for samples prep and standard curve generation often results in samples for mass spectrometric analysis to be analyzed in batch mode. Researchers tend to prefer workflows where samples are accumulated until a level where the effort to generate standard curves and calibrants is amortized by a sufficient number of samples. A downside of this approach is that the turnaround time is dependent on the rate of sample accumulation—if the sample accumulation rate is slow the time to generate results can be long, especially for the samples received early in each batch. While in some applications, the time-to-results for a mass spectrometric analysis may not be important, there are other applications, such as many clinical or healthcare related applications, where the generation of rapid results is critical.

Both immunoassays and mass spectrometry assays have limitations around time-to-answer. Clinical analyzers running immunoassays are highly automated but commonly require 60 to 90 minutes to provide a result. The lack of automation in most mass spectrometry assays adds the requirement of an experienced operator that makes the time-to-answer much more variable. It is common for many mass spectrometry assays to have very long turnaround times. In cases where sample accumulation is slow, the batch mode process often becomes the biggest limiting factor.

SUMMARY OF THE DISCLOSURE

Accordingly, the present disclosure presents novel systems, devices and methods for addressing at least some of the problems associated with current systems and techniques. In some embodiments, an automated system that prepares biological samples and determines the concentration of one or more target analytes via mass spectrometry is provided. The time from sample introduction to the reporting of data, in some embodiments, takes a relatively short amount of time (e.g., several minutes). In some embodiments, a biological sample to be analyzed is a blood sample. For many applications, only a single drop of blood may be sufficient. Through the use of a mixture of standards with unique molecular mass (see above), a quantitative analysis of the target analyte can be performed in a single MS run (for example), eliminating the need to create and analyze standard curves. One advantage of such embodiments, is that it can eliminate the need for batch creation since the requirement to amortize the time and effort of creating and analyzing standard curves can be eliminated.

Some embodiments may be used to quantify the concentration of pharmaceutical compounds, such as antibiotics in blood samples from patients. For example, in some embodiments, only ten (10) microliters of blood (approximately one drop) may be used (which may be obtained via a commercially available finger-prick lancet) and capillary blood collection device. The blood sample may then be delivered to the system according to some embodiments directly from the capillary through the sample port. A schematic outline of the instrument and workflow, according to some embodiments, is shown in FIG. 1.

In some embodiments, an MS system is also provided which eliminates the need to create external calibration curves with standards of known concentrations. Thus, in such embodiments, it is possible to generate accurate analytical results in a short amount of time (e.g., a matter of minutes). In some embodiments, since the system automates sample preparation while eliminating the need to create standard curves, the workflow and hands-on time required to generate results is fast and simple.

Yet another benefit of some embodiments of the present disclosure is streamlined and simplified data management systems. In traditional measurement, where an external calibration curve is used, the instrument data from the test sample alone is not useful. Specifically, the instrument response from the test sample is only meaningful when analyzed in relation to the standard curve generated from the external calibrants. Therefore, the data from the standard curve and the data from the test samples must always be co-analyzed and archived, which adds complexity to data management and storage systems, thus creating additional challenges during data retrieval. According to some embodiments of the disclosure, because all of the data required to accurately calculate the analyte concentration are available within the single injection (i.e., single sample), only a single data file needs to be analyzed and archived greatly reducing the complexity of the data management architecture. A unique sample identifier, such as a bar code, may be all that is required to access a specific mass spectrometer data file containing all of the necessary data.

Another added benefit of some of the embodiments of the present disclosure is simplified sample management. For example, with the traditional approach, each of the external calibration samples, along with the test samples, need to be tracked and loaded into the MS. The order in which samples are analyzed by the MS needs to be properly maintained and requires the creation of an order of analysis in the MS, often referred to as a sample batch. Furthermore, if a sample needs to be reanalyzed at a future point for any reason, the original standard curve also needs to be reanalyzed. Re-analysis of the standard curve together with test samples necessitates the physical storage of all of these samples together requiring some form of sample management and storage system being implemented. According to some embodiments of the present disclosure, because all of the information required for a quantitative measurement is contained within each sample, a simple unique identifier for each test sample (e.g.,: a bar code) is all that is necessary for storage and potential reanalysis.

Still other advantages of some of the embodiments of the present disclosure include:

1) Fast time-to-answer. Even the fastest existing techniques typically take 1 hour or longer to deliver results. If the analysis is performed by a send-out assay (i.e., to a testing service not within the organization) results can take up to a week. Since the trough concentrations of many drugs are measured, the next dose is delivered before the results of the assay are available. In many cases, especially when dealing with critically ill patients, administration of one or more incorrect doses of an essential pharmaceutical while awaiting for blood test results is likely to have a significant negative impact in health outcomes. In sharp contrast, according to some embodiments of the present disclosure, the very next dose can be appropriately adjusted since results are available in near real-time. Furthermore, since each assay is a complete measurement without the requirement for an independent standard curve to be created, some embodiments of the present disclosure offer complete flexibility in analysis compared to traditional batch-mode workflows.

2) Low blood volume. For pediatric and neonatal monitoring available blood volume is a very important consideration. By using a single drop (for example) of blood obtained from a single finger or heel prick, some embodiments of the present disclosure help eliminate this barrier to testing. While in adult patients, blood volume is often not a limitation, the relative comfort of a finger prick over a conventional vacuum tube blood draw is an advantage, especially if multiple samples are required over time.

3) High selectivity and specificity. Compared to immunoassays, in some embodiments of the present disclosure, the mass spectrometry-based assay is able to accurately analyze a wide range of small molecule analytes, including those that have metabolites or related compounds that cross-react with the antibodies used in immunoassays.

4) Ease of developing new assays. According to some embodiments of the present disclosure, the development of mass spectrometry methods for quantifying additional compounds is straightforward and can be done as new compounds are being researched or introduced. The MS according to such embodiments can be optimized through the selection of the appropriate mass-to-charge ratio settings for each analyte. By comparison, in existing technologies, for a new immunoassay a raising and selecting a specific antibody is required—an expensive process that often fails to provide an appropriate solution for small molecule analytes.

5) Ease of data analysis, storage and manipulation. Because all of the information necessary for quantification of each sample is contained within that sample (i.e., no requirement for external standard curves or calibrators), in some embodiments, all of the data required for that measurement is contained within a single data file. Therefore, data analysis and storage as well as sample storage are greatly streamlined which decreases the potential for errors and increases the confidence in the measurement.

Accordingly, in some embodiments, a system for determining the concentration of an analyte of interested in a bodily fluid is provided which comprises a fluid pumping system comprising at least one positive pressure pump and at least one valve for directing fluid flow, a sample preparation portion comprising a disposable cartridge having a sample introduction port, a filtration region, a chromatography region, and an outlet, and a sample analysis portion comprising a mass spectrometer, where the mass spectrometer produces a spectra for an analyte of interest in a sample of a bodily fluid, as well as at least one of a plurality of isotopes of the analyte of interest or a plurality of derivatized samples of the analyte of interest added to the sample in a single spectral measurement. The system may further include at least one processor having operational thereon computer instructions for at least controlling operation of the system, determining a concentration of the analyte contained in the bodily fluid sample, and reporting the at least one analyte concentration.

Such embodiments may also include one and/or another of the following features:
- the fluid pumping system comprises a first pump and a second pump, and the at least one valve comprises a multi-port valve;
- the multi-port valve includes a selector configured to select at least one pair of ports for fluid communication there-between;

the multi-port valve comprises at least 6 ports designated respectively as ports 1 through 6;

upon the selector being in a first position, ports 1 and 2 are in fluid communication, ports 3 and 4 are in fluid communication, and ports 5 and 6 are in fluid communication;

upon the selector being in a second position, ports 2 and 3 are in fluid communication, ports 4 and 5 are in fluid communication, and ports 6 and 1 are in fluid communication;

at least one position of the selector is configured for loading and washing position of the bodily fluid sample;

at least one position of the selector is configured for an elution of the bodily fluid sample;

port 1 is connected to the first pump and port 2 is connected to the sample introduction port;

port 3 is connected to the second pump and port 4 is connected to the mass spectrometer;

port 5 is connected to is connected to the outlet of the cartridge and port 6 is connected to a waste tank;

port 1 is connected to the first pump and port 2 is connected to the sample introduction port, port 3 is connected to the second pump and port 4 is connected to the mass spectrometer, port 5 is connected to is connected to the outlet of the cartridge and port 6 is connected to a waste tank;

the multi-port valve comprises at least 3 ports designated respectively as ports 1 through 3;

upon the selector being in a first position, ports 2 and 3 are in fluid communication;

upon the selector being in a second position, ports 1 and 3 are fluid communication;

the first position is configured for loading and washing position of the bodily fluid sample;

the second position of the selector is configured for elution and mass-spectrometric analysis of the bodily fluid sample;

port 1 is connected to the mass spectrometer;

port 2 is connected to a waste tank; and/or port 3 is connected to is connected to the outlet of the cartridge.

In some embodiments, a system for determining a concentration of an analyte of interest in a bodily fluid is provided which comprises a pumping system including a plurality of different solvents, a sample preparation cartridge, a sample introduction port configured with the sample preparation cartridge, an outlet configured with the sample preparation cartridge, a filtration unit for the removal of insoluble components like cells or platelets configured with the cartridge, a chromatography system for the purification of the analyte of interest along with standards samples, a mass spectrometer, and at least one processor having operational thereon computer instructions for controlling operation of the mass spectrometer, determining a concentration of at least one analyte contained in the sample, and reporting the at least one analyte concentration.

Some embodiments may further include one or more of the following features:

a user interface, where the user interface includes input means for at least one of programing and directing at least one function of the system;

the input means includes a menu which includes selection means for selecting an assay of interest;

upon selection of an assay of interest, the correct mass spectrometry settings for that assay are automatically transferred to the mass spectrometer;

the disposable cartridge is identified for a specific assay; identification comprises at least one of an RFID tag and a one or two-dimensional bar code; and/or upon selection of a specific assay from the menu of available assays, the appropriate disposable cartridge is loaded and verified to the specific assay.

In some embodiments, a method for determining the concentration of an analyte of interest in a bodily fluid is provided and comprises providing an original sample comprising at least one of a blood, urine and saliva of a patient containing the analyte of interest, adding a plurality of stable isotopes of the analyte of interest to the original sample to produce a test sample, wherein each isotope is added at a different concentration, analyzing the test sample via a mass spectrometer such that the plurality of isotopes of the analyte of interest and the original sample are analyzed in a single measurement, creating a standard curve from data produced from the analysis of the single measurement, and calculating the concentration of the analyte of interest of the original sample based upon the standard curve.

In some embodiments, a method for determining the concentration of an analyte of interest in a bodily fluid is provided and comprises providing an original sample comprising at least one of a blood, urine and saliva, the test sample containing the analyte of interest, adding, to the original sample, a plurality chemically derivatized analyte samples to produce a test sample, the derivatized analyte samples being obtained by reacting the analyte of interest with a plurality of different molecules and/or a reacting the analyte of interest with a plurality of different isotopes of the same molecule, analyzing the test sample via a mass spectrometer such that the plurality of derivatized analyte samples and the original sample are analyzed in a single measurement, creating a standard curve of the spectra from the data produced from the single measurement, and calculating the concentration of the analyte of interest in the original sample based upon the standard curve.

The volume of the original sample in such method embodiments (as well as system embodiments) less than about 10 microliters of blood.

In some embodiments, a disposable cartridge for use in a system for determining a concentration of an analyte of interest in a bodily fluid is provided and comprises a housing, a sample introduction port, a filtration unit, and a chromatography system for the purification of the analyte of interest and standards samples.

Such cartridge embodiments may further include one or more of the following features:

the cartridge is manufactured from a bio-inert polymeric material;

the bio-inert polymeric material comprises at least one of polyetheretherketone (PEEK), polypropylene, and polystyrene;

the housing comprises a first upper section and a lower bottom section;

the filtering portion is configured in the upper section;

the chromatography media is configured in the lower section;

the sample introduction port is in fluid communication with a filtrate reservoir;

the sample port is separated from the filtrate reservoir by a asymmetric polysulfone membrane; and/or a bodily fluid sample includes standards samples, where the standards samples diffuse through the membrane such that, upon the bodily fluid sample being blood, platelets, red and white blood cells are trapped within larger pores of the membrane and the liquid portion of the blood sample diffuses through the membrane and is collected in the filtrate reservoir.

In some embodiments, a system for the determination of a concentration of one or more analytes in a fluid including a bodily fluid is provided and comprises a fluid pumping system comprising at least one positive pressure pump and a valve system for diverting fluid flow, a sample preparation portion comprising a removable cartridge, the cartridge including a sample introduction port, a filtration region, and a chromatography region, a sample analysis portion comprising a mass spectrometer, and a processor including computer instructions operating thereon configured to at least one of analyze data, monitor quality of the system, and report results.

These and other embodiments, object, advantage and features of the various disclosed embodiments will become even more evident with reference to the attached figures and details.

FURTHER DETAILS FOR SOME OF THE EMBODIMENTS

Figure 1:
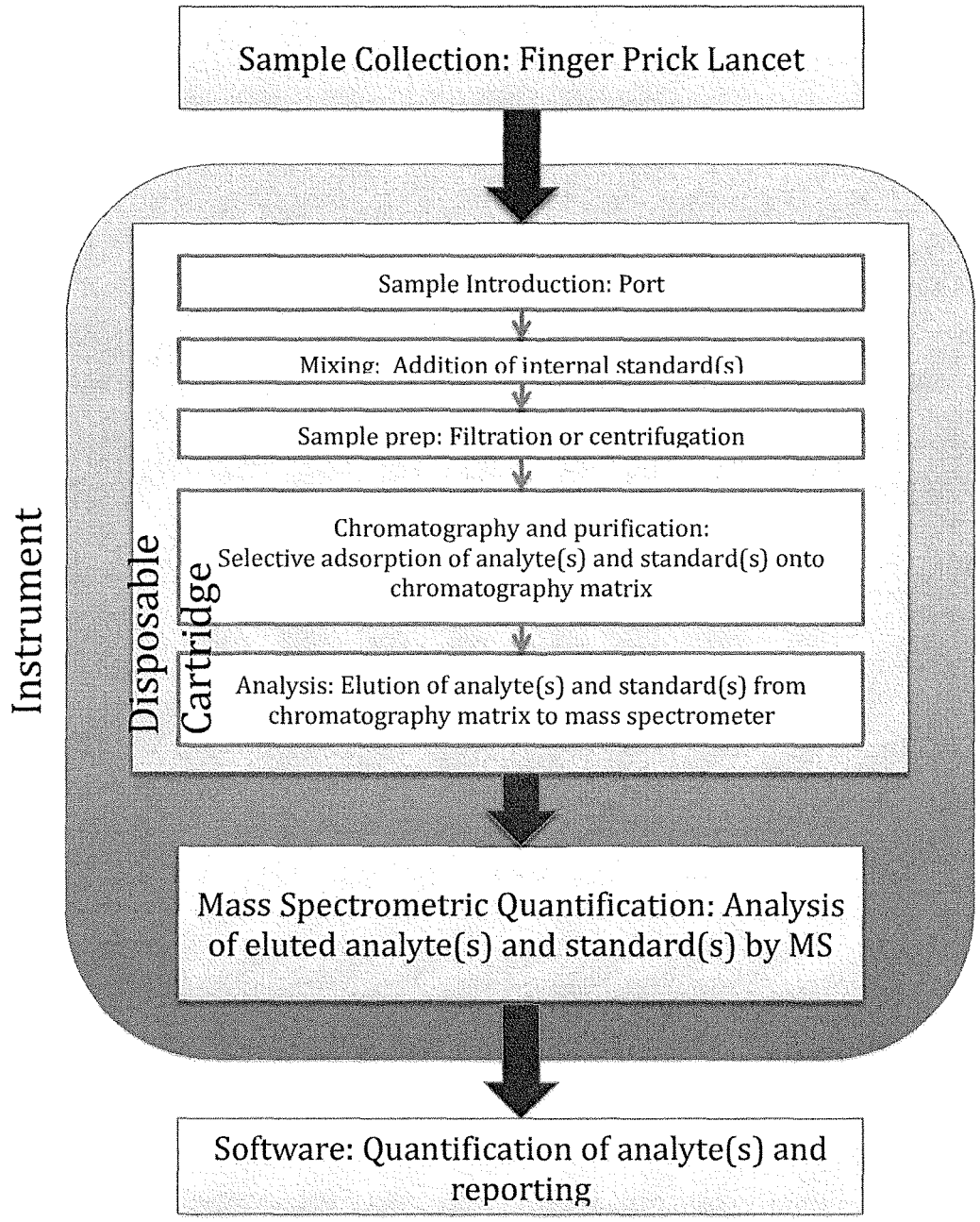
FIG. 1 illustrates a schematic outline of a system and workflow, according to some embodiments of the present disclosure.

Accordingly, the following exemplary embodiments of the various methods, systems and device presented by the current disclosure are provided below.

Internal Standards. Some embodiments of the present disclosure provide an MS system which adds a series of different internal standards at different concentrations to the test sample, which is then analyzed within a single mass-spectrometric measurement. For example, in some embodiments, two or more stable isotopes (i.e., a plurality, in some embodiments, 3 or more) of the analyte of interest may be added to a test sample at different concentrations. A MS may then be used to analyze the three (multiple) stable isotopes together with the analyte of interest in a single measurement. The MS response for each of the stable isotope concentration points may be used to create a standard curve that, in turn, can be used to accurately calculate the concentration of the analyte of interest. In some embodiments, this approach effectively combines the use of internal standards and external calibrants into a single instrument, measurement system.

As indicated, multiple stable isotopes with different molecular mass may be used. For example, a series of hydrogen or carbon$^{12}$ atoms are replaced with deuterium or carbon$^{13}$ atoms. Each stable isotope standard should be at least two mass units apart to minimize interference of naturally occurring $C^{13}$ isotope, especially if the analyte of interest has a large number of carbon atoms. In such cases, a molecular mass separation of three or more units may be required.

In some embodiments, if multiple stable isotope standards with different molecular mass are not available, or are costly or time prohibitive to provide (as chemical synthesis of stable isotopes can be difficult and expensive), a series of standards can be chemically synthesized where the analyte of interest is chemically modified. For example, a small molecule can be reacted with the analyte of interest to create a new molecule with a slightly larger molecular mass. To generate several internal standards with different molecular mass, a series of chemical reactions with different small molecules can be performed. Alternately, the chemical reaction could be performed with a number of stable isotopes of the same small molecule to generate standards.

This approach to generate a series of standards with different molecular mass is to chemically derivatize the analyte of interest with another molecule. There is a wide range of well-established derivatization techniques familiar to those skilled in the art. The derivatization reaction can either be done with a series of reagents with slightly different chemical structure (and therefore molecular mass) or with multiple stable isotopes of the same derivatizing agent.

For example, an amine reactive probe such as an isothiocynate or succinimidyl ester could be used to quickly and efficiently derivatize a primary amine containing molecule such as vancomycin. A series of reactions with similar but slightly different derivatization reagents, (e.g., one additional carbon atom in a carbon chain) could be used to generate a family of standards for vancomycin with very similar properties in the analytical system, but each with a unique molecular mass.

Systems. In some embodiments, a system is provided to conduct MS analysis, which may comprise a pumping system with at least two (2) different solvents (e.g., one for washing the sample over a chromatography media and a second for elution of analytes and standards off of the chromatography media), a sample preparation cartridge (which may be single use, and/or be disposable) which may include a sample introduction port, and a MS for quantification of an analyte(s) of interest and standards. A computer system may also be provided in such a system to control the instrument and/or for the automated quantification and reporting of analyte concentrations.

In some embodiments, the system may include a pumping system having at least two (2) different solutions, a valve module, a cartridge (e.g., disposable) with a sample and standard introduction port, a mechanism to deliver a metered amount of an appropriate amount of internal standard to the sample introduction port, and a MS. Other embodiments of the fluidic system are possible within the scope of this disclosure.

Figure 2:
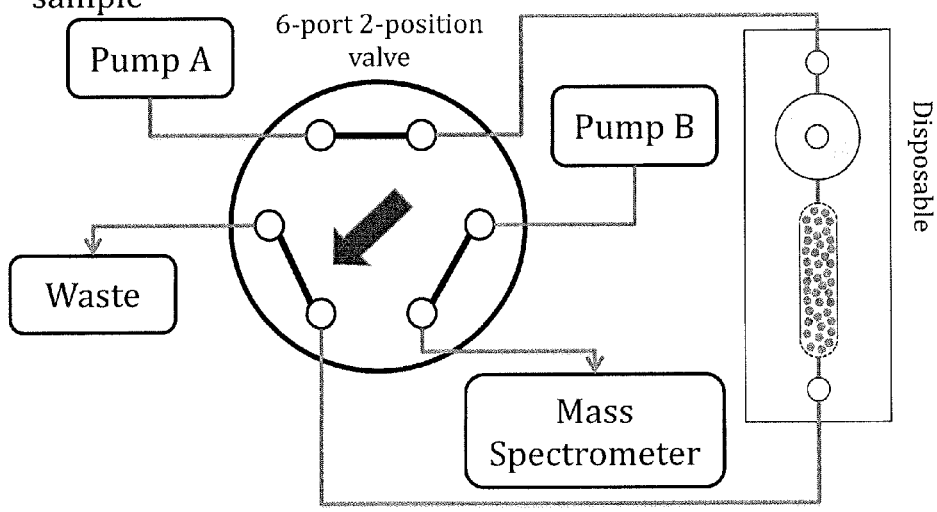
FIG. 2 illustrates an example of a fluidic pathway according to some embodiments of the present disclosure.
Figure 2:
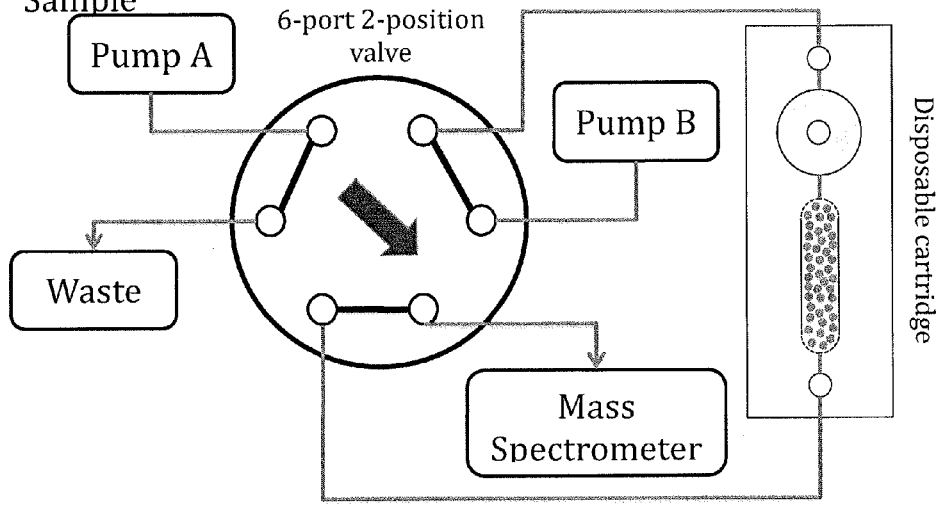

The pumping system may include a plurality, for example, two (2) independent single channel pumps (e.g., isocratic), the cartridge (which may be disposable), and the MS, one or more (and in some embodiments, all) are in fluidic communication through a single 6-port, 2-position valve (for example). An example of a fluidic pathway is shown in FIG. 2. In such an embodiment, a simple, robust, low cost pump(s) may be used. However, in some embodiments, the chromatography may be limited to a two (2) step, solid-phase extraction approach where a single solvent or buffer can be used for the washing and elution steps.

Figure 3:
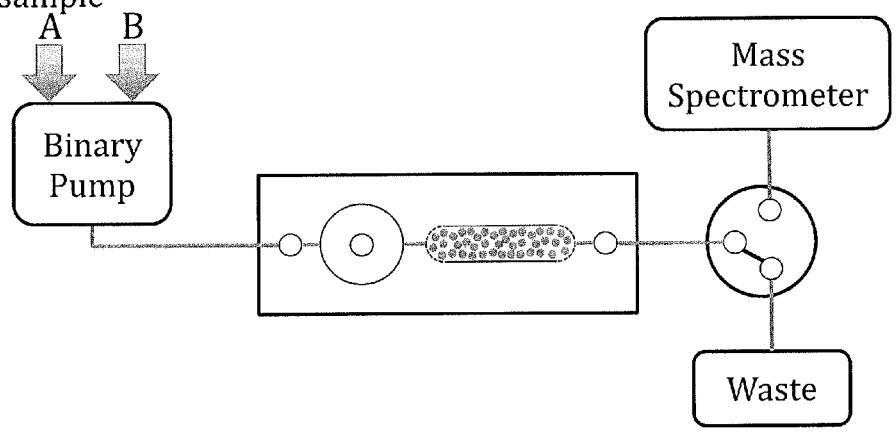
FIG. 3 illustrates a schematic of the fluidic system according to some embodiments of the present disclosure.
Figure 3:
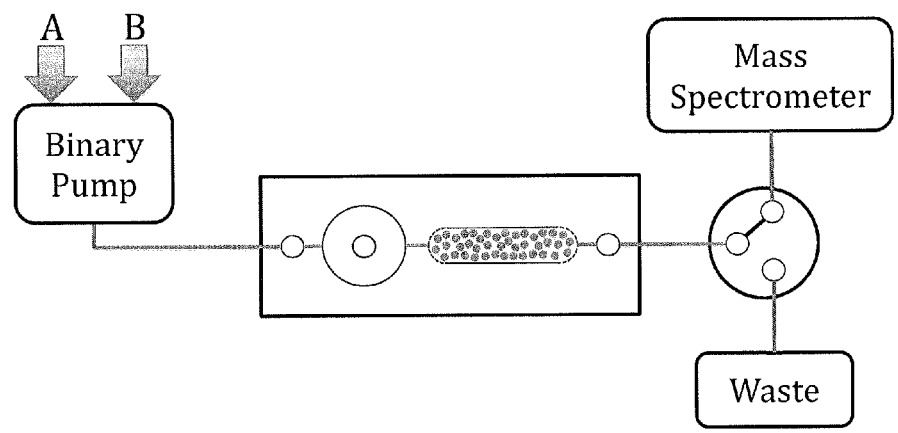

In some embodiments, the pumping system comprises a binary or quaternary pump capable of pumping 2 or more solutions independently or as mixtures (for example). The fluidic system, according to some embodiments, comprises the pumping system, the disposable cartridge, and the MS in fluidic communication through a 3-port, 2-position selection valve (for example). In such embodiments, for example, the presence of a pumping system capable of delivering mixtures of two or more solvents may enable gradient elutions to be performed in which the percentage of an elution solvent is gradually increased over time. As a result, different compounds elute from the chromatography media depending on their partition coefficient for the solvents being used. A schematic of the fluidic system for such embodiments is shown in FIG. 3.

Methods. The following is exemplary of a method for conducting mass-spectromatic analysis of a sample according to some embodiments of the present disclosure, using one and/or another of disclosed system embodiments.

In some embodiments, a sample and internal standards may be added to the sample introduction port when both pumps are inactive. In some embodiments, it is important that the proper internal standards are added to the test sample prior to the analysis. As described earlier, according to some embodiments, the addition of at least one internal standard is used to normalize the instrument response. Through the addition of multiple internal standards, a truly quantitative concentration can be calculated for the analytes of interest (according to some embodiments).

In some embodiments, a metered amount of an organic solvent (e.g., acetonitrile or methanol) containing the appropriate internal standards is added to the sample introduction port and quickly allowed to evaporate. A stream of inert gas (e.g., nitrogen) can be used to help facilitate rapid evaporation of the solvent, leaving behind a solid residue of the internal standards within the sample introduction port. The addition of the liquid test sample (e.g., blood or urine) may solubilize the internal standard prior to sample filtration.

In some embodiments, the appropriate internal standards for a particular assay may be added to the sample introduction port during the manufacturing process in a solid state (for example). Alternately, a metered amount of the internal standards can be added to the sample introduction port of the cartridge during manufacturing in a liquid state (e.g., dissolved in an organic solvent) that is then dried (e.g., evaporated, freeze-dried, or lyophilized) leaving behind solid residue of the internal standards. The solid-state internal standards may then dissolve in the test sample upon addition of the test sample to the sample introduction port. Such an approach, according to some embodiments, implicitly relies that the chemical stability of the solid-state internal standards be determined and may require appropriate storage conditions (e.g., temperature control, protection from light, etc.).

After the sample has been filtered through the asymmetric polysulfone filter/membrane of the cartridge, the sample introduction port may be blocked to prevent flow in the reverse direction, and pump 1, of the exemplary system having two pumps, may be activated while valving is configured in a first position. After an appropriate volume of first solution has been delivered to the chromatography media in the cartridge, pump 1 is inactivated, pump 2 is activated, and the valving is actuated to a second position. Upon actuation of the valving, elution solvent may be delivered from pump 2 to the chromatography media resulting in the analytes being eluted from the chromatography media and into the mass spectrometer for analysis. In some such embodiments, it is recommended that pump 2 be actuated prior to the actuation of valve 2 to establish stable spray within the source of the mass spectrometer.

Salts and mass spectrometry compatible components of the sample may be diverted to a waste area/conduit to protect the MS. Accordingly, valving may be thus configured to divert the eluted sample to the MS once elution solvent is being pumped. One of skill in the art will appreciate that a variety of valving, e.g., diversion valves, may be substituted for the 2-position rotary valve shown in FIG. 3. For example, a microfluidic valve that alternately pinches closed one of the two flow paths can be used without altering the function of the device.

The chromatography step, according to some embodiments, can be performed using many different commercially available solid-phase materials. For example, a very wide range of chromatography media are available and include silica-based coated particles, polymeric materials, and others. Phases can be reverse phase (e.g., hydrophobic) or normal phase (e.g., hydrophilic or ionic) and can incorporate a wide range of different chemistries including but not limited to C4, C8, C18, phenyl, cyano, HILIC, graphitic carbon, and others. The exact nature of the chromatography media can be optimized for the specific analytes of interest and cartridges containing different types of chromatography media may be developed for different applications or analytes. In some embodiments, the chromatography media may be retained in place within the cartridge through the use of narrow channels, for example, which may be machined, molded, or printed directly into the substrate of the cartridge. By using a chromatography media having particles larger than these narrow channels, the media can be immobilized within the appropriate region of the cartridge without the need for frits or filters (for example).

In some embodiments, rather than a two-step chromatography system (i.e., aqueous followed by organic), an increasing percentage of organic solvent over time can be delivered to the chromatography media. This type of chromatographic elution is known as a gradient elution and can be used to selectively elute specific analytes from the chromatography media.

Figure 4:
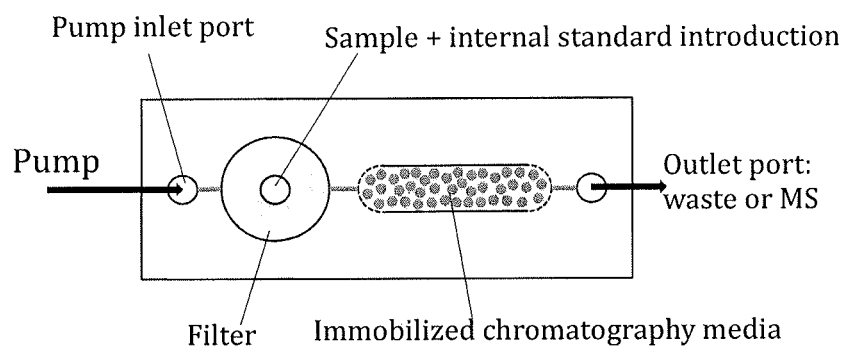
FIG. 4 illustrates top and side views of a sample cartridge according to some embodiments of the present disclosure.
Figure 4:
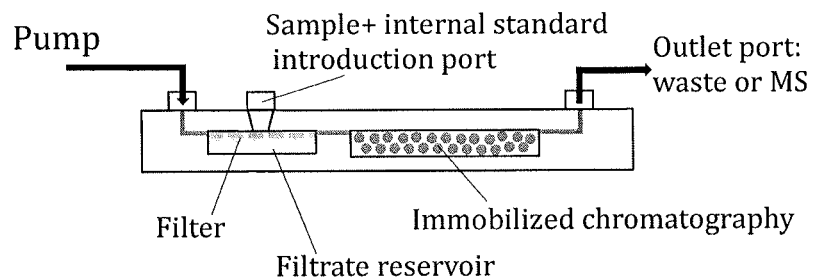

Cartridges. In some embodiments, the sample preparation cartridge is provided (see above), which may be disposable and may include the port for sample introduction and(or) the addition of one or more standards. The cartridge may also include a filtration unit for the removal of insoluble components like cells or platelets, and may further include a chromatography system for the purification of the analyte(s) of interest along with the internal standard(s). Top and side views of the cartridge (according to some embodiments) which may be used within the instrument are shown in FIG. 4. In some embodiments, each cartridge may be used a single time for each analysis and discarded.

In some embodiments, such a single-use disposable cartridge provides advantages over multi-use systems including, for example, the elimination of potential carryover from one sample to the next, and the elimination of concerns over degradation of the chromatography media due to problems like clogging (e.g., particulates or precipitates in the sample) and/or irreversible binding of various matrix components (e.g., lipids or steroids).

In some embodiments of the cartridge, a filter or membrane is provided within the cartridge which may be manufactured from commercially available material such as asymmetric polysulfone. One such filter commercialized by the Pall Corporation under the "Vivid™" trade name is designed specifically for the separation of plasma from whole blood. Similar membranes and filters are also available from other manufacturers. The filter or membrane may be used to capture larger components in a fluid sample (e.g., platelets, red and white blood cells, and the like), being captured by larger pores thereof, while plasma containing an analyte(s) of interest flows down through smaller pores on the downstream side (for example). When a bodily fluid sample including the appropriate internal standards is introduced at the sample port, the platelets and cells within the blood sample are trapped within the filter/membrane and plasma containing the analyte(s) of interest along with the internal standards is collected within a filtrate reservoir.

Cartridge Manufacture. In some embodiments, cartridges may be manufactured from a bio-inert polymeric material such as polyetheretherketone (PEEK), polypropylene, polystyrene, or a similar polymer. When selecting a material for the cartridge factors such as the ability to mold, machine, or print the components; cost; and/or biological compatibility may be considered. For at least some embodiments, it is particularly important that the analytes of interest do not have a high affinity for binding to the material used in the cartridge. Adhesion or binding of analyte to the cartridge itself could result in lower instrument signal and could lead to inaccurate results. It may be possible to optimize the material for a specific application and use different types of cartridges for different analytes (for example).

To facilitate manufacturing of the cartridge, in some embodiments, a bottom portion of the cartridge that contains the fluidic channels, the filtrate reservoir, and/or chromatography matrix, is separately manufactured from an upper portion that includes ports for interfacing to the pumping system, sample introduction, and/or detector. Features may alternately be machined into the bottom portion, or the unit may be injection molded or manufactured from additive manufacturing (i.e., 3-dimensional printing).

Figure 5:
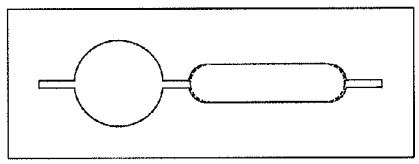
FIG. 5 illustrates exemplary designs for two sections of a sample cartridge according to some embodiments of the present disclosure.
Figure 5:
Figure 5:
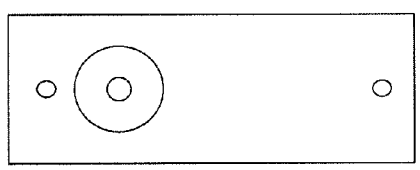
Figure 5:
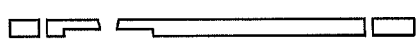
Figure 5:
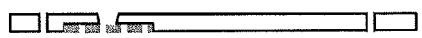
Figure 5:
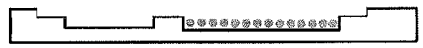
Figure 5:

FIG. 5 shows exemplary designs for two sections of a cartridge device according to some embodiments. In such embodiments, the filter/membrane may be attached to the upper section and the chromatography media may be placed in the lower section.

In some embodiments, once the filter/membrane has been attached and appropriate chromatography matrix have been added, the manufacture of the cartridge can be completed by fusion of the two sections (e.g., bottom and top sections). The fusion may be accomplished thermally, through irradiation with an ultraviolet light, or via an adhesive (for example). Alternately, features that clip and hold the two portions together could be added to the two components eliminating the need for an adhesive altogether.

Once the two sections are fused, the open grooves in the first (e.g., lower) section may become enclosed channels establishing fluidic communication between the various sections of the cartridge. The through holes in the second (e.g., upper) section become ports to establish fluidic communication to the pumping system, the sample introduction port, and the mass spectrometer. Features may be molded or machined into a respective section to help facilitate leaktight fluidic connections, for example, a commercially available "Luer-Lock" or similar taper union-type fitting may be used. Other types of standard fittings are also available and well known to those skilled in the art. The fluidic channels formed by fusion of the two sections may include an internal diameter of about 0.01 inches (~250 micron), for example. Depending on the application, smaller internal diameters of about 0.005 inches (~125 micron) or larger internal diameters may be used. The internal diameter may be a function of the readily available sample volume and desired back pressure within the system and may be optimized for a specific application and analyte.

In some embodiments, the cartridge may include an additional feature(s) that facilitates the blocking of the sample introduction port after the filtration step is complete. Blocking of the sample introduction port may be accomplished by plugging the port mechanically or by other means (for example). In some embodiments, the blocking off of the sample introduction port keeps the appropriate solvents traveling through the chromatography media rather than back out of the sample introduction port in the reverse direction once the pumping system is activated.

Computer System/Processor and Control. The system for MS analysis according to some embodiments may be controlled via one or more computer processors having computer instructions operating thereon to effect an algorithm (for example) for the automated mechanical, fluidic, and/or control operations for performing (and completing) a quantitative measurement. The mechanical operations may include actuation of one or more valves, control of one or more pumps, mechanical positioning of certain elements, and/or the control of the MS for the acquisition of analytical data.

User Interface. Computer systems for the MS system according to some embodiments of the disclosure may further include a user interface through which an operator can program and direct one or more functions or operations thereof (for example). In some such embodiments, the user interface allows for correct setup for an appropriate assay. To that end, in such embodiments, such correct setup enables the correct data to be obtained from an assay the correct cartridge being used, as well as the correct MS settings. In some embodiments, a user need only select the assay of interest from a menu of assays available on a user interface. Thereafter, upon selection of a given assay, the correct mass spectrometry settings for that assay are automatically transferred to the MS.

System Control Configuration. In some embodiments, the cartridge for the system may be identified as being appropriate only for a specific assay. Such identification may be through a radio frequency ID tag and/or a one or two-dimensional bar code. Once the user has selected a specific assay from a menu of available assays through the user interface, and a disposable cartridge has been automatically or manually loaded into the system, the system may verify that the specific identifier on the disposable cartridge matches the assay selected by the user. If the two assays are in conflict, an error message or warning may be issued alerting the user of the discrepancy. If the selected assay is in concordance with the loaded cartridge, the user may be informed and the correct mass spectrometry settings can be transferred to the MS.

Data Analysis. In some embodiments, once the mass spectrometric information is acquired, a computer processor (s)(which may be the processor which controls the MS system) may be used to compare the instrument signal for each of the internal standards as well as the analyte(s) of interest. A standard curve may be created using the instrument response for each of the known concentrations of the internal standards. This curve may be, in turn, used to calculate the unknown concentration of the analyte in the test sample.

Quality Control. In some embodiments, it may be possible (and desirable) to incorporate multiple levels of error checking and quality control into a data analysis algorithm, operational on one or more processors (e.g., of the system). For example, and according to some embodiments:

the linearity of the instrument response versus the known concentration of the standards can be mathematically determined and compared to preset limits;

the overall instrument response in terms of signal-to-noise ratio or absolute signal can be calculated for each internal standard and compared versus acceptable responses; and/or more complicated mass spectrometric parameters such as peak shape, symmetry, tailing, and the like, can also be determined and compared to acceptable benchmarks.

Accordingly, if any such calculated parameters fall outside acceptable limits, the system may be configured to display (or otherwise report) an error or warning message indicating that the calculated concentration of the analyte may be inaccurate.

Data Reporting. In some embodiments, data reporting (system and/or sample characteristics, control, data analysis, results, etc.) may be available at two different layers. For example, in an instrument run in which no errors are present, the system can display the concentration of the test analytes in the patient blood sample along with a patient identifier such as a name or barcode. In some embodiments, the analyte concentration can be displayed in relation to the desired concentration range, for example, the target concentration range for an antibiotic drug. Additionally, a second level of data can be made available, that displays the raw mass spectrometric data from the instrument along with all of the mathematical calculations performed to derive the final result. Such a level of data and results may be required if there is an error or warning flag displayed by the algorithm requiring further inspection from an operator.

Various implementations of the embodiments disclosed above, in particular at least some of the processes discussed, may be realized in digital electronic circuitry, integrated circuitry, specially designed ASICs (application specific integrated circuits), computer hardware (as noted above), firmware, software (as noted above), and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions for a programmable processor, for example, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor and the like) for displaying information to the user and a keyboard and/or a pointing device (e.g., a mouse or a trackball) by which the user may provide input to the computer. For example, this program can be stored, executed and operated by the dispensing unit, remote control, personal computer (PC), laptop, smartphone, media player or personal data assistant ("PDA"). Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system according to some such embodiments described above may include clients and servers. A client and server are generally remote from each other and typically interact through a communication network. The relationship of client and server arises by virtue of computer programs running on the respective computers and having a client-server relationship to each other.

For example, such a system may include at least one molecule detecting/identification device which is in communication (wired or wireless) with at least one controller/processor. The processor may include computer instructions operating thereon for accomplishing any and all of the methods and processes disclosed in the present disclosure. Input/output means may also be included, and can be any such input/output means known in the art (e.g., display, memory, database, printer, keyboard, microphone, speaker, transceiver, and the like). Moreover, in some embodiments, the processor and at least the database can be contained in a personal computer or client computer which may operate and/or collect data from the detecting device. The processor also may communicate with other computers via a network (e.g., intranet, internet).

EXAMPLES

Example 1

Determination of Vancomycin concentration in plasma samples by mass spectrometry without the need for an external calibration curve. Traditional mass spectrometric quantification of the concentration of anti-infective agent vancomycin in the plasma of a patient would require multiple steps:

1. A sample of plasma not containing any vancomycin is spiked with a known concentration of vancomycin.

2. A dilution series of this sample is prepared in the same plasma matrix to generate a series of samples with different but known concentrations of vancomycin to generate the external standard curve.

3. An internal standard, e.g., a stable isotope of vancomycin, is added to all of the external standard curve samples with known vancomycin concentrations as well as the test sample with unknown vancomycin concentration.

4. All samples (including the external calibration samples and the test sample) are analyzed by an appropriate mass spectrometer where the instrument response for both vancomycin and the internal standard in each of the test and calibration samples is recorded.

5. The MS instrument response for vancomycin for each sample is normalized to the MS instrument response for the internal standard to account for any instrument or sample-specific variability.

6. The MS instrument response for each of the calibration standards with known vancomycin concentration is used to generate a standard curve that in turn can be used to calculate the unknown concentration of vancomycin in the test sample.

The workflow for some embodiments of the present disclosure for this example can be much simpler in comparison:

1) A mixture of a plurality of different stable isotopes of vancomycin (e.g., 3, and in some embodiments, at least 4), each at a different but known concentration, is added to the plasma sample to be analyzed.

2) A single test sample with unknown concentration of vancomycin and the 4 stable isotopes of known concentration (for example) is analyzed in a single (for example) MS measurement where the instrument response for vancomycin and the 4 stable isotopes is recorded.

3) A calibration curve generated to form the 4 stable isotope internal standards (e.g., with respect to the current example) with known concentration and the unknown concentration of vancomycin can be accurately determined, all in a single (for example) MS measurement. In some embodiments, since a single measurement may be used to generate a standard curve and quantify vancomycin concentrations, instrument or sample-specific variability can be automatically accounted for.

Example 2

Determination of Vancomycin concentration in blood samples from a premature infant. Vancomycin is a drug that is commonly used to treat infections from many Gram positive infections. In newborn infants, particularly premature births or in babies with very low birth weight, sepsis is a major cause of morbidity and mortality. For staphylococcal infections vancomycin is the preferred treatment. However, the pharmacokinetics of vancomycin differs in neonates as compared to adults and also show significant inter-neonate variability. Vancomycin concentrations are routinely monitored due to the known toxicity of this drug. An established target for vancomycin is a through plasma concentration of 15-20 µg/ml.

There are commercially available immunoassay tests for vancomycin that are routinely used for the therapeutic drug monitoring of this antibiotic. However, the commercially available tests suffer from several drawbacks. The tests typically require several hundred microliters of blood to be drawn from the patient. This is not a limitation in adults, but in pediatric and neonatal cases available blood volume presents a significant challenge. The total blood volume for all required testing in a neonate is typically 5 mL/kg. For a 500 g neonate, this corresponds to just 2500 µl A over several days making the availability of blood for various laboratory tests a major limitation. Furthermore, most commercially available tests require 60 to 90 minutes to provide an answer. Typically, the trough concentration of vancomycin that is measured and a blood sample is obtained 30 minutes prior to the next dose of the drug. Given the time-to-result of at least 60 minutes for the current assays (and often significantly longer due) it is impossible to adjust the next dose of vancomycin since it is scheduled for administration 30 minutes after the blood draw. As a result, the neonate may be given an incorrect dose for another dosing cycle, possibly more depending on the turnaround time.

According to some embodiments, and with respect to the current example, a 10 microliter blood sample is obtained from a patient using a commercially available heparinized heel-prick lancet and blood collection system 30 minutes prior to the scheduled administration of the next dose of vancomycin. The blood sample is put into the system (according to such embodiments), where the blood sample is transferred to the sample introduction port. Simultaneously, a metered volume of a mixture of internal standards of vancomycin is also transferred to the sample introduction port. The mixture of internal standards contains 4 (i.e., multiple) different chemically derivatized versions of vancomycin, each of the 4 having a slightly larger molecular mass.

In such embodiments, the sample introduction port is in fluidic communication with a filtrate reservoir, but separated by a highly asymmetric polysulfone membrane. The blood sample containing the internal standards diffuses through the membrane where the platelets, red and white blood cells are trapped within the larger pores of the membrane and the liquid portion of the blood sample diffuses through the membrane and is collected in the filtrate reservoir.

Once the plasma separation step is complete, the sample introduction port is mechanically blocked to prevent backflow of sample or liquid in a reverse direction. A first pump containing an aqueous buffer acidified with a mixture of 0.01% trifluoroacetic acid and 0.09% acetic acid is activated. The pump is connected to the disposable cartridge through a first pump port and is in fluidic communication with the filtrate reservoir. The sample in the filtrate reservoir is pushed through the action of this pump through another channel to another region within the cartridge containing an immobilized chromatography media. In this case, chromatography media consisting of 40 micron diameter silica beads that have a surface derivatized with an 4-carbon long chain is used (i.e., C4 reverse phase media).

As the plasma sample is pushed through the chromatography media, the vancomycin standards along with any vancomycin present in the sample are adsorbed onto and retained by the cartridge. However, the salts and many of the proteins present in the sample are not adsorbed and are flushed through the chromatography media to an outlet port to a waste container. The adsorbed sample is washed by a minimum of 10 volumes of aqueous buffer (for example) to ensure that the majority of salt and protein in the sample are removed.

Next, the first pump is stopped and a second pump containing an organic buffer of acetonitrile acidified with 0.01% trifluoroacetic acid and 0.09% formic acid (for example) is activated. This pump is also in fluidic communication with the disposable cartridge through yet another pump port. Simultaneously with the activation of the second pump, a valve is actuated within the instrument that establishes fluidic communication between the outlet port of the cartridge and the mass spectrometer. This port was previously in communication with a waste container. The organic solvent is flowed over the chromatography media which results in the vancomycin and the 4 internal standards to desorb off of the chromatography media and dissolve in the organic solvent. This solvent containing vancomycin and the internal standards is delivered to the mass spectrometer where each of the 5 compounds (vancomycin plus the 4 standards) are quantified. The mass spectrometer used is a triple quadrupole system with an atmospheric pressure ion source operating in positive electrospray ionization mode.

The mass spectrometric results are delivered to a data analysis algorithm that converts the instrument response factor to a 4-point calibration curve. The relative instrument response for each of the 4 internal standards with known concentrations is used to quickly create the calibration curve. The calibration curve can be used to convert the instrument response for vancomycin to an accurate concentration of the analyte through the use of an automated computer algorithm.

Example 3

Determination of the concentration of the antibiotic agent Colistin in the blood of a critically ill patient. Colistin (trade name: Colomycin®) is an anti-infective agent effective against many Gram negative bacteria. Colistin was initially discovered in the late 1940s. It is a pharmaceutical agent that was used in a very limited manner for decades due to the fact that the drug is severely nephrotoxic. Newer drugs have much preferable safety profiles and as a result colistin was used only in very rare situations for many decades. Colistin has a therapeutic range of zero—it is toxic at every dose, including the therapeutic dose. However, recently colistin has been found to be the only effective treatment against many multidrug resistant Pseudomonas and Acinetobacter bacteria species. As a result, the use of colistin as a last-line anti-infective agent has become common, despite the well-characterized toxicity of the drug. Even in cases where a successful health outcome against the infectious agent is achieved, the nephroptoxicity of the drug often results in irreversible kidney damage. Many patients require dialysis, sometimes indefinitely.

Accurately dosing critically ill patients is particularly challenging since in such patients altered kidney function and increased volume of distribution is very common. The kidneys may shut down resulting in lower than usual clearance, or may become hyper-active resulting in rapid drug elimination. Furthermore, patients may be on fluid treatment that can further dilute the effective drug concentration in the plasma. As a result, trying to estimate the actual plasma concentration of colistin in an individual patient can be very challenging.

In this example, a bacterial swab from a critically ill patient in an Intensive Care Unit is taken and cultured. The infectious agent is identified as an Acinetobacter and since previous treatment attempts by antibiotic agents with cleaner toxicity profiles has failed, colistin is prescribed as the course of treatment. The in vitro minimum inhibitory concentration (MIC) of colistin is determined by culturing the isolated bacteria in media containing different concentration of colistin using a commercially available bacterial resistance kit.

Colistin is administered to the patient intravenously. At 30 minutes after the initiation of treatment a 10 µl blood sample is obtained from the patient via a finger prick blood collection and presented to the device described in the system according to some embodiments, via the sample introduction port of the cartridge. The device has already been preloaded (for example) with the appropriate cartridge and standard mixture for monitoring the drug colistin. Using such embodiments, the systemic concentration of colistin in plasma of the patient is calculated in a matter of minutes. Additional blood samples are obtained at 60, 90, 150, and 300 minutes after initiation of the infusion of colistin and the plasma drug concentration is measured similarly at these additional time points.

The system, according to some embodiments, may be configured (e.g., via software, one or more processors) to generate a pharmacokinetic plot for colistin based on the time versus plasma drug concentration data that is obtained from the above measurements. An objective is to assure that the plasma concentration of colistin is at least as high as the in vitro MIC level determined previously. It is highly unlikely that the treatment will result in arresting bacterial growth or in bacterial killing at plasma concentrations below the established MIC. The result of low colistin concentrations will likely result in a dose that is not efficacious and a positive treatment outcome will be in jeopardy. Similarly, it is important that the colistin concentration not reach levels well above the MIC due to the dose-related toxicity of colistin.

Based on the pharmacokinetic data generated by the device and the target concentration of colistin (i.e., the MIC), the antibiotic drug can be accurately titrated for the patient, according to some embodiments. In cases where the plasma concentration is below the MIC, the dose of the drug and/or the dosing frequency can be increased. Similarly, if the plasma concentration of colistin is significantly above the MIC, an adjustment with lower doses and/or a less frequent dosing regimen can be utilized.

Example 4

Patient-specific titration of the chemotherapy drug busulfan in chronic myeloid leukemia patients receiving bone marrow transplantation. Busulfan (trade name: Myleran®) is an alkylating antineoplastic agent used in the treatment of chronic myeloid leukemia (CML). Busulfan is often used as a conditioning agent in bone marrow transplantation. It often administered intravenously with the total dose being divided equally over 4 consecutive days, though there are multiple dosing regimens used. Busulfan has many side effects including pulmonary fibrosis (busulfan lung) and others. There is also significant patient-to-patient variability in metabolism and hence plasma levels of the drug. As a result, the plasma busulfan levels are routinely monitored to ensure drug concentrations are within the therapeutic window. Most monitoring is performed via HPLC-MS techniques.

In this example, a patient is dosed with busulfan intravenously. A total of six 10 microliter blood samples are collected via a finger-prick method at 30 minute intervals after the dosing of the drug is completed. Accordingly, using at least some embodiments of the present disclosure, immediately after the collection of each sample, the blood is introduced via the sample introduction port (of the cartridge) into the system of such embodiments. The system is equipped with a disposable cartridge designed for busulfan analysis. An internal standard mixture consisting of a mixture of 4 different stable isotopes of busulfan at different but known concentrations is added to the blood sample within the sample introduction port. The concentration of busulfan in each of the 6 samples is determined as described.

In such embodiments, the time versus busulfan plasma concentration may be used to create a pharmacokinetic plot. A goal is to achieve a 6-hour area under the curve (AUC) of between 900 and 1500 micromoles of busulfan. AUC (6-hour) higher than 1500 micromoles is associated with toxicity while those below 900 micromoles may result in incomplete bone marrow ablation. Based on the data provided by the current invention the complete pharmacokinetic profile can be determined after the initial dose, and any adjustments to dosing can be made prior to the second dose. Conventional mass spectrometry assays often take many hours or even days to complete. For drugs such as busulfan that are administered over several days, knowing the plasma concentration is critical. If the results of the blood plasma concentration aren't available for days, dose adjustment can only be made in the final day or days of the treatment regimen. A patient may be receiving a toxic or sub-efficacious dose for the bulk of the treatment course which is likely to have a negative impact on the health outcome.

Any and all references to publications or other documents, including but not limited to, patents, patent applications, articles, webpages, books, and the like, presented in the present application, are herein incorporated by reference in their entirety.

Example embodiments of devices, systems, and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices, which may further include any and all elements from any other disclosed methods, systems, and devices. In other words, elements from one and/or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure).

What is claimed is:

1. A system for determining the concentration of an analyte of interest in a bodily fluid, the system comprising:
   a fluid pumping system comprising at least one positive pressure pump;
   a sample preparation portion comprising a single-use, disposable cartridge comprising:
      a solid residue of a plurality of internal standards within a sample introduction port, the plurality of internal standards comprising a plurality of stable isotopes of the analyte of interest or a plurality of chemically derivatized analyte samples, each of the plurality of internal standards being at different, known concentrations;
      a filtration region;
      a chromatography region; and
      an outlet port configured to be in fluid communication with a mass spectrometer;
   a sample analysis portion comprising the mass spectrometer, wherein the mass spectrometer produces a spectra for the analyte of interest in a sample of a bodily fluid, and at least one of the plurality of internal standards in a single spectral measurement; and
   at least one processor having operational thereon computer instructions for at least controlling operation of the system, creating a standard curve of the spectra, and determining a concentration of the analyte of interest contained in the bodily fluid sample based upon the standard curve, and reporting the at least one analyte concentration.

2. The system of claim 1, wherein fluid pumping system comprises a first pump and a second pump and at least one valve for directing fluid flow, and wherein the at least one valve comprises a multi-port valve.

3. The system of claim 2, wherein the multi-port valve includes a selector configured to select at least one pair of ports for fluid communication there-between.

4. The system of claim 3, wherein the multi-port valve comprises at least 6 ports designated respectively as ports 1 through 6.

5. The system of claim 4, wherein upon the selector being in a first position, ports 1 and 2 are in fluid communication, ports 3 and 4 are in fluid communication, and ports 5 and 6 are in fluid communication.

6. The system of claim 5, wherein upon the selector being in a second position, ports 2 and 3 are in fluid communication, ports 4 and 5 are in fluid communication, and ports 6 and 1 are in fluid communication.

7. The system according to claim 3, wherein at least one position of the selector is configured for loading and washing position of the bodily fluid sample.

8. The system according to claim 3, wherein at least one position of the selector is configured for an elution of the bodily fluid sample.

9. The system of claim 4, wherein port 1 is connected to the first pump and port 2 is connected to the sample introduction port.

10. The system of claim 4, wherein port 3 is connected to the second pump and port 4 is connected to the mass spectrometer.

11. The system of claim 4, wherein port 5 is connected to is connected to the outlet of the cartridge and port 6 is connected to a waste tank.

12. The system of claim 4, wherein port 1 is connected to the first pump and port 2 is connected to the sample introduction port, port 3 is connected to the second pump and port 4 is connected to the mass spectrometer, port 5 is connected to is connected to the outlet of the cartridge and port 6 is connected to a waste tank.

13. The system of claim 3, wherein the multi-port valve comprises at least 3 ports designated respectively as ports 1 through 3.

14. The system of claim 13, wherein upon the selector being in a first position, ports 2 and 3 are in fluid communication.

15. The system of claim 14, wherein upon the selector being in a second position, ports 1 and 3 are in fluid communication.

16. The system according to claim 14, wherein the first position is configured for loading and washing position of the bodily fluid sample.

17. The system according to claim 15, wherein the second position of the selector is configured for elution and mass-spectrometric analysis of the bodily fluid sample.

18. The system of claim 13, wherein port 1 is connected to the mass spectrometer.

19. The system of claim 13, wherein port 2 is connected to a waste tank.

20. The system of claim 13, wherein port 3 is connected to is connected to the outlet of the cartridge.

* * * * *